United States Patent [19]
Nelson et al.

[11] 3,975,540
[45] Aug. 17, 1976

[54] 2-SUBSTITUTED-5-OXO-5H-DIBENZO(a,d)-CYCLOHEPTENES, AND DERIVATIVES THEREOF, AND METHODS AND COMPOSITIONS FOR THE USE THEREOF

[75] Inventors: Peter H. Nelson; Karl G. Untch, both of Los Altos, Calif.

[73] Assignee: Syntex (U.S.A.) Inc., Palo Alto, Calif.

[22] Filed: Apr. 28, 1975

[21] Appl. No.: 572,477

[52] U.S. Cl. .............................. 424/315; 260/503; 260/590 FB; 260/554; 260/570.5 R; 260/570.5 C; 424/327; 424/331
[51] Int. Cl.[2] .................................. A61K 31/185
[58] Field of Search .............. 260/503, 511, 590 FB

[56] References Cited
UNITED STATES PATENTS

| | | | |
|---|---|---|---|
| 3,372,192 | 3/1968 | Engelhardt | 260/590 FB |
| 3,478,048 | 11/1969 | Edenhofer et al. | 260/590 X |
| 3,551,498 | 12/1970 | Tristram et al. | 260/590 FB |
| 3,697,581 | 10/1972 | Hummer | 260/590 FB |
| 3,833,655 | 9/1974 | Edenhofer et al. | 260/590 FB |
| 3,836,585 | 9/1974 | Tristram et al. | 260/511 |
| 3,883,592 | 5/1975 | Berezin et al. | 260/590 |

*Primary Examiner*—James O. Thomas, Jr.
*Assistant Examiner*—James H. Reamer
*Attorney, Agent, or Firm*—Joseph I. Hirsch; William B. Walker

[57] ABSTRACT

2-Substituted-5-oxo-5H-dibenzo[a,d]cycloheptenes represented by the following formula:

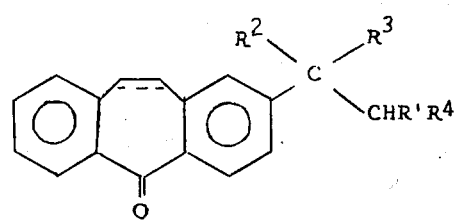

where one of $R^2$ and $R^3$ is hydrogen, and the other is hydrogen, methyl, or ethyl, or together $R^2$ and $R^3$ are methylene; and $R'$ and $R^4$ are alkoxy, or together $R'$ and $R^4$ are =O, =NOH, =NNHCONH$_2$, or alkylenedioxy of the formula —O—CH$_2$—(CR$^5{}_2$)$_n$—CH$_2$—O— where $n_5$ is 0—2, $R^5$ is hydrogen or methyl when $n$ is 1, and $R^5$ is hydrogen when $n$ is 2, or one of $R'$ and $R^4$ is —OH and the other is (SO$_3$Y) where Y is sodium or potassium. The compounds have anti-inflammatory, analgesic and anti-pyretic activities and, accordingly, are useful in the treatment of inflammation, pain and pyrexia.

37 Claims, No Drawings

2-SUBSTITUTED-5-OXO-5H-DIBENZO(a,d)CYCLOHEPTENES, AND DERIVATIVES THEREOF, AND METHODS AND COMPOSITIONS FOR THE USE THEREOF

FIELD OF THE INVENTION

This invention relates to novel chemical compounds. More particularly, this invention relates to novel pharmaceutically active 5-oxo-5H-dibenzo[a,d]cycloheptene derivatives substituted at the 2-position with an ethanal moiety or an α-substituted ethanal moiety, the acetal and alkylenedioxy derivatives thereof, the bisulfite salts, oximes and semicarbazones thereof.

SUMMARY OF THE INVENTION

The novel 5-oxo-5H-dibenzo[a,d]cycloheptene-2-substituted compounds of the present invention can be represented by the following formula:

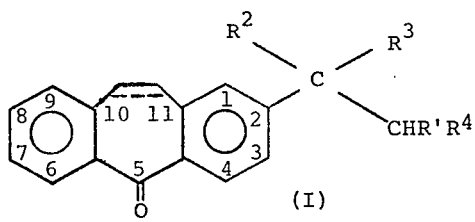

where one of $R^2$ and $R^3$ is hydrogen, and the other is hydrogen, methyl, or ethyl, or together $R^2$ and $R^3$ are methylene; and R' and $R^4$ are alkoxy, or together R' and $R^4$ are =O, =NOH, =NNHCONH$_2$, or alkylenedioxy of the formula —O—CH$_2$—(CR$^5_2$)$_n$—CH$_2$—O— where n is 0–2, $R^5$ is hydrogen or methyl when n is 1, and $R^5$ is hydrogen when n is 2, or one of R' and $R^4$ is -OH and the other is (SO$_3$Y) where Y is sodium or potassium.

As used in the specification and claims, the term "alkoxy" refers to those groups having the formula $R^6$O- where $R^6$ is a straight or branched chain alkyl group having 1 to 6 carbon atoms. Typical alkoxy groups include, for example, methoxy, ethoxy, propoxy, butoxy, 3-pentoxy, and the like. Alkylenedioxy is intended to include ethylenedioxy, 1,3-propylenedioxy, 2,2-dimethylpropylenedioxy, 1,4-butylenedioxy, and the like.

The 2-substituted-10,11-dihydro-5-oxo-5H-dibenzo[a,d]cycloheptenes of this invention may also be referred to as the corresponding 2-substituted-5-oxo-5H-dibenzo[a,d]cycloheptanes, it being understood that both designations refer to the compounds of Formula I where there is a single bond between the carbon atoms at the 10- and 11-positions.

When one of $R^2$ and $R^3$ is hydrogen and the other is methyl or ethyl, the compounds of Formula I exist as pairs of enantiomorphs. Each enantiomorph or optical isomer and mixtures thereof are included within the present invention. The compounds of Formula I which exist as pairs of enantiomorphs can be administered as racemic mixtures or they can be administered as resolved enantiomorphs. In some instances, one enantiomorph exhibits greater anti-inflammatory, analgesic and/or anti-pyretic activity than the other corresponding enantiomorph.

The optical isomers can be resolved by conventional means, such as selective biological degradation, or by the preparation of the corresponding carboxylic acid followed by the preparation of the diastereoisomer salts thereof with an optically active base, such as l-amphetamine, separation of the diastereoisomer salts by fractional crystallization, cleaving to form the optically resolved isomers(s) of the carboxylic acid, converting the resolved carboxylic acid isomer to the corresponding resolved acid chloride and then preparing the resolved aldehyde therefrom. Optionally, the resolved aldehyde can be made from the corresponding resolved alcohol; however, the resolved aldehyde so produced and the respective resolved starting material will not necessarily have the same optical rotation, although they will have the same absolute configuration. For example, (d) 2-(5-oxo-5H-dibenzo[a,d]-cyclohepten-2-yl)propanal is obtained from (d) 2-(5-oxo-5H-dibenzo[a,d]cyclohepten-2-yl)propionic acid, while (d) 2-(5-oxo-5H-dibenzo[a,d]cycloheptan-2-yl)propanal is obtained from (1) 2-(5-oxo-5H-dibenzo[a,d]cycloheptan-2-yl)propanol.

The compounds of Formula I exhibit anti-inflammatory, analgesic and anti-pyretic activities. Accordingly, the compositions of this invention are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formula I in an appropriate pharmaceutical composition can be via any of the accepted modes of administration of agents for the treatment of inflammation, pain, or pyrexia. Thus, administration can be, for example, orally, parenterally, per os, or topically, in the form of solid, semi-solid or liquid dosage forms, such as, for example, tablets, suppositories, pills, capsules, ointments, or the like, preferably in unit dosage forms suitable for simple administration of precise dosages. The compositions of this invention will include a conventional pharmaceutical carrier or excipient and an active compound of Formula I, and, in addition, may include other medicinal agents, pharmaceutical agents, carriers, adjuvants, etc.

The preferred manner of administration is oral using a convenient daily dosage regimen which can be adjusted according to the degree of affliction. Generally, a daily dose of from 0.1 mg. to 50 mg. of the active compound of Formula I per kilogram of body weight is used. Most conditions respond to treatment comprising a dosage level on the order of 1 mg. to 10 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compounds of Formula I may be formulated into a suppository using, for example, polyalkylene glycols, for example, polypropylene glycol, as the carrier. Liquid pharmaceutically administerable compositions can, for example, be prepared by dissolving, dispersing, etc., an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's *Pharmaceutical Sciences*, Mack Publishing Company, Easton, Pennsylvania, 14th. Edition, 1970. The composition to be administered will, in any event, contain a quantity of the active compound(s) in a pharmaceutically effective amount of relief of the particular condition being treated in accordance with the teachings of this invention.

The compounds of Formula I (where $R'$ and $R^4$ together are —O) can be prepared by converting the corresponding alkanoic acid, for example, 2-(5-oxo-5H-dibenzo[a,d]cyclohepten-2-yl)propionic acid, to the corresponding acid halide, for example, 2-(5-oxo-5H-dibenzo[a,d]cyclohepten-2-yl)propionyl chloride as by treatment at room temperature with thionyl chloride and dimethylformamide in chloroform, and then reducing the acid chloride, as with lithium aluminum tritertiarybutoxy hydride, at about −100°C to about 0°C, generally about −80°C, for about ¼ hour to about 10 hours, generally, about 2 hours or so, in an inert organic solvent, such as diglyme, ether, tetrahydrofuran, monoglyme, and the like. The product aldehyde is then isolated and purified according to standard procedures known to those skilled in this art.

The alkanoic acid compounds referred to above are prepared by conducting an Arndt-Eistert reaction upon 5-oxo-5H-dibenzo[a,d]cyclohepten-2-carboxylic acid to afford (5-oxo-5H-dibenzo[a,d]cyclohepten-2-yl)acetic acid or 2-(5-oxo-5H-dibenzo[a,d]cyclohepten-2-yl)propionic acid. in similar manner starting with 5-oxo-10,11-dihydro-5H-dibenzo[a,d]cycloheptene-2-carboxylic acid, the corresponding 5-oxo-5H-dibenzo[a,d]cycloheptane-2-alkanoic acids are prepared.

5-Oxo-5H-dibenzo[a,d]cycloheptene-2-carboxylic acid is prepared by esterifying 2-methylterephthalic acid with methanol, in the presence of acid catalyst, to afford the corresponding dimethyl ester which, in turn, is reacted with N-bromosuccinimide to afford 2-bromomethylterephthalic acid dimethyl ester. This diester is reacted with triphenylphosphine to afford 2,5-bis(carbomthoxy)benzyltriphenyl-phosphonium bromide which is treated with benzaldehyde and diazabicylononene, to afford, after alkaline hydroylsis, cis and trans stilbene 2,5-dicarboxylic acid. Hydrogenation of this latter compound with hydrogen over a 5% palladium on carbon catalyst affords 2-(2-phenethyl)terephthalic acid. Treatment with polyphosphoric acid yields 5-oxo-5H-dibenzo[a,d]-cycloheptane-2-carboxylic acid which can be recrystallized from aqueous dimethylformamide. 5-Oxo-5H-dibenzo[a,d]cycloheptene-2-carboxylic acid is prepared by successively treating 5-oxo-5H-dibenzo[a,d]cycloheptane-2-carboxylic acid with diazomethane, N-bromosuccinimide, and dimethylformamide/diazabicyclononene, followed by base hydrolysis and acidification.

In the Arndt-Eistert reaction, the carboxylic chain of the starting 2-carboxylic acid compound is elongated by treating the 2-carboxy compound with thionyl chloride to obtain the acid chloride. This acid chloride is reacted with diazomethane to form a diazoketone which is rearranged by the action of a silver salt in the presence of an alcohol, for example, methanol or ethanol. The resultant alkyl ester of the 2-acetic acid compound can be hydrolyzed to afford the free 2-acetic acid. Or, the resultant compound can be treated with an alkali metal hydride, amide, or dialkyl amide, such as sodium hydride, lithium diisopropyl amide or sodium dimethyl amide, followed by treatment with an alkyl halide, such as methyl iodide or ethyl iodide, to α-alkylate the 2-acetic acid ester compound, thereby forming the corresponding 2-propionic acid ester or the 2-butyric acid ester, which also can be hydrolyzed to form the corresponding 2-propionic acid or 2-butyric acid compounds, respectively. Optionally, the 2-propionic acid compound can be prepared, without the need for α-methylation, by reacting 2-chloroformyl-5-oxo-5H-dibenzo[a,d]cycloheptene with ethereal diazoethane, followed by treatment with N,N-dimethylaniline and benzyl alcohol, base hydrolysis and acidification. The Arndt-Eistert reaction is well-known series of steps, the particulars of which can be determined by reference to the Examples below or to the articles thereon in the published literature.

The compounds of Formula I (where $R'$ and $R^4$ together form =O) can also be prepared by treating the corresponding alcohol, for example 2-(5-oxo-5H-dibenzo[a,d]cyclohepten-2-yl)ethan-1-ol or 2-(5-oxo-5H-dibenzo[a,d]cyclohepten-2-yl)-propan-1-ol, or the corresponding 10,11-dihydro compounds, with an oxidizing agent, such as chromium trioxide, at about 0°–40°C, generally at about 25°C, for about 1 minute to about 3 hours, generally about 5 minutes or so, in an inert organic solvent, such as acetone, pyridine, methylene dichloride, and the like. The product compound is then isolated and purified according to standard procedures known to those skilled in this art. This procedure is suitable for preparing the α,α-methylene compounds by preparation of the 2-substituted-prop-1-en-3-ol compounds followed by oxidation with chromimum trioxide.

The starting alcohols are prepared by treating the corresponding alkanoic acid, for example 2-(5-oxo-5H-dibenzo[a,d]-cyclohepten-2-yl)propionic acid, the corresponding 10,11-dihydro compound, or an alkyl ester thereof, with lithium aluminum hydride at about 0°C to the boiling point of the reaction medium, preferably about room temperature, for about ¼ hour to about 4 hours, generally about 1 hour or so, in an inert organic ether, such as diethyl ether, dipropyl ether, diisopropyl ether, dibutyl ether, glyme, tetrahydrofuran, and the like. The ethereal solution, after addition of water, separation and filtration, is treated with manganese dioxide at about 0°C to about the boiling point of the reaction medium, also preferably about room temperature, for about 2 to about 24 hours, generally about 8 hours or so.

The acetals of this invention, that is, the compounds of Formula I where $R'$ and $R^4$ are alkoxy, are prepared by treating the aldehydes of Formula I with alkanols having 1 to 6 carbon atoms, such as methanol, ethanol, n-propanol, i-propanol, n-butanol, i-butanol, n-pentanol, i-pentanol, n-hexanol, i-hexanol, and the like, in the presence of a catalyst, such as ammonium nitrate, ferric chloride, perchloric acid and the like. The cyclic acetals are prepared utilizing ethylene glycol, 1,3-propylene glycol, 2,2-dimethylpropylene glycol or 1,4-butanediol and the like, in the presence of an acid catalyst such as p-toluene sulfonic acid, perchloric acid, etc.

The bisulfite addition derivatives of the aldehydes of Formula I are prepared by treating the aldehyde product with a saturated aqueous solution of sodium (or potassium) bisulfite to afford those products of Formula I where one of R' and $R^4$ is -OH and the other is $SO_3Y$ where Y is sodium or potassium.

The oximes of Formula I (where R' and $R^4$ together form =NOH) and the semicarbazones of formula I (where R'and $R^4$ together form =NNHCONH$_2$) are prepared by condensing the aldehyde with hydroxylamine or semicarbazide, respectively, with conditions, etc., that are known to those skilled in this art.

In each of the process steps, described herein above and below, unless otherwise indicated, the respective intermediate products are preferably separated from the reaction mixture and purified prior to their use as starting materials for the next step in the process. Such separation and purification can e effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give th compound desired. In view of this disclosure, the preparation of particular compounds, including compounds falling within the present invention but not specifically described in this specification, will be apparent to those skilled in this art.

Exemplary of the compounds of the present invention, as represented by the structural formula above, are the following illustrative compounds:

(5-oxo-5H-dibenzo[a,d]cyclohepten-2-yl)ethanal;
2-(5-oxo-5H-dibenzo[a,d]cyclohepten-2-yl)propanal;
2-(5-oxo-5H-dibenzo[a,d]cyclohepten-2yl)butanal;
2-(5-oxo-5H-dibenzo[a,d]cyclohepten-2-yl)propenal;
1,1-dimethoxy-2-(5-oxo-5H-dibenzo[a,d]cyclohepten-2-yl)-ethane;
1,1-diethoxy-2-(5-oxo-5H-dibenzo[a,d]cyclohepten-2-yl)-ethane;
1,1-dipropoxy-2-(5-oxo-5H-dibenzo[a,d]cyclohepten-2-yl)ethane;
1,1-dimethoxy-2-(5-oxo-5H-dibenzo[a,d]cyclohepten-2-yl)-propane;
1,1-diethoxy-2-(5-oxo-5H-dibenzo[a,d]cyclohepten-2-yl)propane;
1,1-dipropoxy-2-(5-oxo-5H-dibenzo[a,d]cyclohepten-2-yl)propane;
1,1-diethoxy-2-(5-oxo-5H-dibenzo[a,d]cyclohepten-2-yl)butane;
1,1-diethoxy-2-(5-oxo-5H-dibenzo[a,d]cyclohepten-2-yl)prop-2-ene;
1,1-ethylenedioxy-2-(5-oxo-5H-dibenzo[a,d]cyclohepten-2-yl)propane;
1,1-(1,3-propylenedioxy)-2-(5-oxo-5H-dibenzo[a,d]-cyclohepten-2-yl)propane;
sodium bisulfite addition product of 2-(5-oxo-5H-dibenzo[a,d]cyclohepten-2-yl)propanal;
potassium bisulfite addition product of 2-(5-oxo-5H-dibenzo[a,d]cyclohepten-2yl)propanal;
(5-oxo-5H-dibenzo[a,d]cyclohepten-2-yl)ethanal;
2-(5-oxo-5H-dibenzo[a,d]cycloheptan-2-yl)propanal;
2-(5-oxo-5H-dibenzo[a,d]cycloheptan-2-yl)butanal;
2-(5H-dibenzo[a,d]cycloheptan-2-yl)propenal;
1,1-dimethoxy-2-(5-oxo-5H-dibenzo[a,d]cycloheptan-2-yl)ethane;
1,1-diethoxy-2-(5-oxo-5H-dibenzo[a,d]cycloheptan-2-yl)ethane;
1,1-dipropoxy-2-(5-oxo-5H-dibenzo[a,d]cycloheptan-2-yl)ethane;
1,1-dimethoxy-2-(5-oxo-5H-dibenzo[a,d]cycloheptan-2-yl)propane;
1,1-diethoxy-2-(5-oxo-5H-dibenzo[a,d]cycloheptan-2yl)propane;
1,1-dipropoxy-2-(5-oxo-5;l H-dibenzo[a,d]cycloheptan-2-yl)propane;
1,1-diethoxy-2-(5-oxo-5H-dibenzo[a,d]cycloheptan-2-yl)butane;
1,1-diethoxy-2-(5-oxo-5H-dibenzo[a,d]cycloheptan-2-yl)prop-2-ene;
1,1-ethylenedioxy-2-(5-oxo-5H-dibenzo[a,d]cyclocycloheptan-2-yl)propane;
1,1-(1,3-propylenedioxy)-2-(5-oxo-5H-dibenzo[a,d-]cycloheptan-2-yl)propane;
sodium bisulfite addition product of 2-(5-oxo-5H-dibenzo[a,d]cycloheptan-2-yl)propanal;
potassium bisulfite addition product of 2-(5-oxo-5H-dibenzo[a,d]cycloheptan-2-yl)propanal;
2-(5-oxo-5H-dibenzo[a,d]cyclohepten-2-yl)propionaldehyde oxime;
2-(5H-dibenzo[a,d]cyclohepten-2-yl)propionaldehyde semicarbazone;
2-(5-oxo-5H-dibenzo[a,d]cycloheptan-2-yl)propionaldehyde oxime;
2-(5-oxo-5H-dibenzo[a,d]cycloheptan-2-yl)propionaldehyde semicarbazone;

and the corresponding l and d isomers of those compounds which have an assymetric carbon atoms.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

Preparation 1

148 G. of 2-methylterephthalic acid is refluxed for 24 hrs. in 750 ml. of dry methanol containing 30 ml. of sulphuric acid. The solution is cooled, poured into water and extracted with ether. The extract is washed, dried and evaporated to give dimethyl-2-methylterephthalate.

88 G. of dimethyl-2-methylterephthalate in 1000 ml. of carbon tetrachloride containing 89 g. (1 eq.) of N-bromosuccinimide is refluxed for 3 hours using a heat lamp. The solution is cooled, filtered and evaporated to dryness to give dimethyl-2-bromomethylterephthalate.

25.7 G. of dimethyl-2-bromomethylterephthalate is refluxed in 250 ml. of acetonitrile containing 26.2 g. (1 eq.) of triphenylphosphine for 4 hrs. The solution is cooled and diluted with 1250 ml. of ether thereby precipitating 2,5-bis(carbomethoxy)-benzyltriphenylphosphonium bromide which is filtered off and dried under vacuum.

51.9 G. of 2,5-bis(carbomethoxy)-benzyltriphenylphosphonium bromide and 10.6 g. of benzaldehyde are stirred in 300 ml. of acetonitrile and 12.4 g. of diazabicyclononene is added. The mixture is heated briefly to reflux, then cooled and evaporated to an oil. The oil is dissolved in ethyl acetate, and the solution washed with dilute hydrochloric acid, dried and evaporated. The residue is refluxed for 12 hrs. in a solution of 20 g. of potassium hydroxide in 300 ml. of water and 50 ml. of methanol. The solution is cooled and extracted with chloroform. The aqueous solution is acidified with dilute hydrochloric acid and the precipitated cis and trans stilbene-2,5-dicarboxylic acid is filtered off and dried.

23.6 G. of cis and trans-stilbene-2,5-dicarboxylic acid is dissolved in 100 ml. of dimethylformamide containing 500 mg. of 5% palladium on carbon and hydrogenated for 2 hrs. The solution is filtered and evaporated to dryness to give a crude product which upon recrystallization from aqueous ethanol yields 2-(2-phenethyl)terephthalic acid.

23.8 G of 2-(2-phenethyl)terephthalic acid is dissolved in 200 ml. of sulpholane at 130° C and 150 ml. of polyphosphonic acid is added with stirring. The mixture is stirred at 130° C for 4 hrs., then poured into 1000 ml. of water. The product is filtered off and recrystallized from aqueous dimethylformamide to yield 5-oxo-5H-dibenzo[a,d]-cycloheptane-2-carboxylic acid (m.p. 203°–204°C).

PREPARATION 2

5.0 G. of 5-oxo-5H-dibenzo[a,d]cycloheptane-2-carboxylic acid (as prepared in Preparation 1 above) is suspended in 50 ml. of dioxane, added to excess ethereal diazomethane, and stirred until dissolution is complete. The solution is then evaporated to dryness to yield 2-carbomethoxy-5-oxo-5H-dibenzo[a,d]cycloheptane.

4.68 G. of 2-carbomethoxy-5-oxo-5H-dibenzo[a,d]cycloheptane is refluxed in 100 ml. of carbon tetrachloride containing 3.56 g. (1 eq.) of N-bromosuccinimide while being irradiated with a 100 watt incandescent lamp. After 2 hrs. the solution is cooled, filtered and evaporated to dryness. The residue is dissolved in 30 ml. of dimethylformamide and 2.48 g. (1 eq.) of diazabicylononene is added. The mixture is heated briefly to 60° C, and water and ethyl acetate are added. The organic layer is washed with dilute hydrochloric acid and water, then dried and evaporated to give 2-carbomethoxy-5-oxo-5H-dibenzo[a,d]cycloheptene. Hydrolysis in eight to one aqueous methanol, 5% potassium hydroxide, followed by acidification with dilute hydrochloric acid yields 5-oxo-5H-dibenzo[a,d]-cycloheptene-2-carboxylic acid (m.p. 261°–262°C).

Preparation 3

22 G. of 5-oxo-5H-dibenzo[a,d]cycloheptene-2-carboxylic acid is stirred in 200 ml. of chloroform, 50 ml. of thionyl chloride and 1 ml. of dimethylformamide for 8 hrs. The mixture is evaporated to dryness and the residue recrystallized from acetonitrile to yield 2-chloroformyl-5-oxo-5H-dibenzo[a,d]cycloheptene. This is dissolved in 200 ml. of chloroform and added to a 3-fold excess of ethereal diazomethane at 0°C. The mixture is left at 0°C for 12 hrs. then evaporated to dryness. The residue is recrystallized from acetonitrile to yield 2-diazoacetyl-5-oxo-5H-dibenzo-[a,d]cycloheptene. The diazoketone is heated to reflux in 250 ml. of ethanol and a saturated triethylamine solution of 2 g. of silver benzoate is added slowly until gas evolution ceases. The solution is cooled, filtered and evaporated to yield ethyl (5-oxo-5H-dibenzo[a,d]cyclohepten-2-yl)acetate. This ester is refluxed in 5% aqueous potassium hydroxide for 12 hrs. The solution is cooled, acidified with dilute hydrochloric acid and extracted with ether. The ether extract is dried and evaporated to yield (5-oxo-5H-dibenzo[a,d]cyclohepten-2-yl)acetic acid which can be recrystallized from acetone-hexane (m.p 148°–149.5°C).

Preparation 4

Lithium isopropylcyclohexylamide is prepared by adding 10 mls. 1.0 molar n-butyl lithium to a solution of 1.41 g. of isopropylcyclohexylamine in 100 ml. of dry tetrahydrofuran. To this solution, cooled to −80°C, there is added a solution of 2.94 g. of ethyl (5-oxo-5H-dibenzo[a,d]cyclohepten-2-yl)acetate (as prepared in Preparation 3 above) in 10 ml. of tetrahydrofuran. The mixture is left for 5 minutes, then 1.42 g. of methyl iodide is added. The reaction mixture is allowed to attain room temperature, then water and ether are added. The ethereal layer is washed with dilute hydrochloric acid and water, dried and evaporated to yield ethyl 2-(5-oxo-5H-dibenzo[a,d]cyclohepten-2-yl)propionate. This ethyl ester is refluxed for 12 hrs. in 5% aqueous potassium hydroxide, followed by acidification with dilute hydrochloric acid and ether extraction to afford dl 2-(5-oxo-5H-dibenzo[a,d]cyclohepten-2-yl)propionic acid (m.p. 138°–139°C, 113°–115°C). This mixture of optical isomers can exist in two crystalline forms. The form having the higher melting point is obtained by using chloroform/hexane as the recrystallizing solvent, while the form having the lower melting point is obtained by using acetone/hexane as the recrystallizing solvent.

Preparation 5

1.075 Ml. of 1.6 molar n-butyllithium in hexane is added to a solution of 0.242 ml. of diisopropylamine in 15 ml. of dry tetrahydrofuran. 0.300 Ml. of hexamethylphosphoric triamide is added and the mixture is cooled to about −60°C. 0.465 G. of methyl (5-oxo-5H-dibenzo[a,d]cyclohepten-2-yl)acetate is added, and after 15 minutes, 0.137 ml. of ethyl iodide is added. The mixture is warmed slowly to room temperature and a further 0.05 ml. of ethyl iodide is added. After 30 minutes an additional 0.05 ml. of ethyl iodide is added. After 30 minutes, a few drops of methanol are added, and then ether and water are added. The organic layer is washed with water, dilute hydrochloric acid and saturated sodium chloride solution, then dried and evaporated to yield the impure product, which, after chromatography on 40 g. silica gel, eluting with hexane:ether (5:1) affords methyl 2-(5-oxo-5H-dibenzo-[a,d]cyclohepten-2-yl)butyrate. 0.326 G. of methyl 2-(5-oxo-5H-dibenzo[a,d]cyclohepten-2-yl)butyrate is refluxed for 4 hours in 10 ml. of methanol and 20 ml. of water containing 0.5 g. of sodium hydroxide. The mixture is cooled, washed with ether and acidifed with dilute hydrochloric acid. The product is extracted with ether and the extract washed, dried and evaporated to yield 2-(5-oxo-5H-dibenzo[a,d]cyclohepten-2-yl)butyric acid (m.p. 147°–148°C).

Preparation 6

In similar manner to the procedure of Preparations 3-5, substituting 5-oxo-5H-dibenzo[a,d]cycloheptane-2-carboxylic acid for 5-oxo-5H-dibenzo[a,d]cyclohepten-2-carboxylic acid, (5-oxo-5H-dibenzo[a,d]cycloheptan-2-yl)acetic acid, 2-(5-oxo-5H-dibenzo[a,d]cycloheptan-2-yl)propionic acid, and 2-(5-oxo-5H-dibenzo[a,d]cycloheptan-2-yl)butyric acid are prepared.

Preparation 7

2.78 G. (0.01 mole) of 2-(5-oxo-5H-dibenzo[a,d]cyclohepten-2-yl)propionic acid is dissolved in 25 ml. of isopropanol and 1.35 g. (0.01 mole) of 1-amphetamine is added. The salt crystallizes out and is filtered off and recrystallized several times to constant specific rotation. The salt is suspended in ether and dilute hydrochloric acid is added. After shaking, the organic layer is washed, dried and evaporated to give d 2-(5-oxo-5H-dibenzo[a,d]cyclohepten-2-yl)propionic acid [m.p. 108-110°C; $[\alpha]_D$ + 48.9° (chloroform)] which can be recrystallized from acetone-hexane. 1 2-(5-Oxo-5H-dibenzo[a,d]cyclohepten-2-yl)propionic acid can be obtained in similar manner using d-amphetamine.

Preparation 8

2.78 G. of 2-(5-oxo-5H-dibenzo[a,d]cyclohepten-2-yl)propionic acid is stirred in a mixture of 20 ml. of benzene and 5 ml. of trifluoroacetic anhydride for 15 minutes. The mixture is evaporated to dryness and redissolved in 20 ml. of dry benzene. A mixture of 1.0 g. of pyridine and 2.44 g. (2 moles) of (+) α-phenylethanol is added. The mixture is left for 30 minutes and then water and ether is added. The organic layer is washed with dilute hydrochloric acid and water, then dried and evaporated. The residue is chromatographed on 100 g. silica gel, eluting with hexane:ether (4:1) to afford a 1:1 mixture of diastereomeric esters. Repeated crystallization of this mixture from ether-hexane yields the less soluble isomers. The purity of samples from successive recrystallizations is monitored by gas-liquid chromatography using a 1 meter × 2 mm. column packed with Chromosorb W (Regis Chemical Co., Chicago, Ill.) impregnated with 3% w/w OV101 polymeric material (Applied Sciences Laboratory, Inc., State College, Penn.) as stationary phase, and helium as the carrier gas at 220°C. The less soluble isomer is decomposed by stirring in a mixture of 5 ml. of benzene and 5 ml. of trifluoroacetic acid for 30 minutes. Water and ether are added and the ethereal layer washed with water, and then with dilute aqueous sodium carbonate. The aqueous layer is acidified with dilute hydrochloric acid and then extracted with ether. The ethereal layer is washed, dried and evaporated to give d 3-(5-oxo-5H-dibenzo[a,d]cyclohepten-2-yl)propionic acid. 1 2-(5-Oxo-5H-dibenzo[a,d]cyclohepten-2yl)propionic acid [m.p. 105°–107°C; $[\alpha]_D$ −47.4° (chloroform)] can be obtained in similar manner using (−) α-phenylethanol.

Preparation 9

2.8 G. (0.01 mole) of 2-(5-oxo-5H-dibenzo[a,d]cycloheptan-2-yl)propionic acid is dissolved in 25 ml. of isopropanol and 1.35 g. (0.01 mole) of l-amphetamine is added. The salt crystallizes out and is filtered off and recrystallized several times to constant specific rotation. The salt is suspended in ether and dilute hydrochloric is added. After shaking, the organic layer is washed, dried and evaporated to give d 2-(5-oxo-5H-dibenzo[a,d]cycloheptan-2-yl)propionic acid (m.p. 100.5°–102°C; $[\alpha]_D$ + 45.2°) which can be recrystallized from acetone-hexane. 1 2-(5-Oxo-5H-dibenzo[a,d]cycloheptan-2-yl) propionic acid (m.p. 103°–104°C; $[\alpha]_D$ −47.6°) can be obtained in similar manner using d-amphetamine.

Preparation 10

1.0 G. of 2-(5-oxo-5H-dibenzo[a,d]cyclohepten-2-yl)propionic acid is dissolved in 25 ml. of chloroform, and 1 ml. of thionyl chloride and 0.1 ml. of dimethylformamide are added thereto. The mixture is left for 1 hour then evaporated under high vacuum to afford 2-(5-oxo-5H-dibenzo[a,d]cyclohepten-2-yl)propionyl chloride. In similar manner, substituting the acids prepared in Preparations 3 and 5–9 for the 2-5-oxo-5H-dibenzo[a,d]cyclohepten-2yl)propionic acid used above, the corresponding acid chlorides are prepared.

Preparation 11

0.5 G. of lithium aluminum hydride is added to a solution of 2.78 g. of 2-(5-oxo-5H-dibenzo[a,d]cyclohepten-2-yl)propionic acid in 200 ml. of anhydrous ether. The mixture is stirred for 2 hours and then excess hydride is destroyed by sequential addition of ethyl acetate, methanol and water. The ethereal solution is separated and filtered and to it is added 15 g. of activated manganese dioxide. The mixture is stirred for 8 hours, then filtered through 10 g. of silica gel and the elute evaporated to afford 2-(5-oxo-5H-dibenzo[a,d]cyclohepten-2-yl)propan-1-ol (m.p. 63°–66°C).

In similar manner substituting:
(5-oxo-5H-dibenzo[a,d]cyclohepten-2-yl)acetic acid,
2-(5-oxo-5H-dibenzo[a,d]cyclohepten-2-yl)butyric acid,
(5-oxo-5H-dibenzo[a,d]cycloheptan-2-yl)acetic acid,
2-(5-oxo-5H-dibenzo[a,d]cycloheptan-2-yl)propionic acid; or
2-(5-oxo-5H-dibenzo[a,d]cycloheptan-2-yl)butyric acid, for the 2-(5H-dibenzo[a,d]cycloheptan-2-yl)propionic acid, the following are prepared:
2-(5H-dibenzo[a,d]cyclohepten-2-yl) ethan-1-ol,
2-(5-oxo-5H-dibenzo[a,d]cyclohepten-2-yl) butan-1-ol,
2-(5-oxo-5H-dibenzo[a,d]cycloheptan-2-yl)ethan-1-ol,
2-(5-oxo-5H-dibenzo[a,d]cycloheptan-2-yl)propan-1-ol, and
3-(5-oxo-5H-dibenzo[a,d]cycloheptan-2-yl)butan-1-ol, respectively.

Preparation 12

A solution of 2.50 g. of 2-carboxy-5-oxo-5H-dibenzo[a,d]cycloheptene in 50 ml. of chloroform, 10 ml. of thionyl chloride and 0.3 ml. of dimethylformamide is stirred for 8 hours, then evaporated to dryness and the residue recrystallized from acetonitrile to yield 2-chloroformyl-5-oxo-5H-dibenzo[a,d]cucloheptene. This is dissolved in 50 ml. of chloroform and added to a 3-fold excess of ethereal diazomethane at 0°C. After 12 hours, the solution is evaporated to dryness and the residue recrystallized from acetonitrile to yield 2-diazoacetyl-5-oxo-5-oxo-5H-dibenzo[a,d]cycloheptene. A solution of 1.37 g. of the latter compound in 50 ml. of tetrahydrofuran is added to 10 ml. of 0.1 N sulfuric acid containing 0.5 g. of copper powder. The mixture is refluxed for 3 hours and then cooled, filtered and poured into water. The solution is extracted with ethyl acetate and the extract washed, dried and evaporated to yield 2-hydroxyacetyl-5-oxo-5H-dibenzo[a,d]cycloheptene which is recrystallized from chloroform/hexane. A solution of 0.05 g. of cupric acetate monohydrate in 5 ml. of acetic acid is heated to 100°C and 3.0 g. of granular zinc is added. The mixture is shaken for 3 minutes and the acetic acid is then decanted. The residual zinc-copper couple is washed three times with 5 ml. portions of acetic acid, then three times with 5 ml. portions of ether. It is then refluxed for four hours under nitrogen in 20 ml. of ether containing 2.5 ml. of methylene iodide, 1.32 g. of 2-hydroxyacetyl-5-oxo-5-H-dibenzo[a,d]cycloheptene is added, and reflux is continued for a further four hours. The mixture is cooled and diluted with 50 ml. of benzene. The liquid phase is decanted and washed with water and aqueous sodium bisulfate, then dried and evaporated. The residue is chromatographed on 50 gm. of silica gel, eluting with ethyl acetate/hexane, to yield 2-(5-oxo-5H-dibenzo[a,d]-cyclohepten-2-yl)prop-1-en-3-ol.

In similar manner substituting 2-carboxy-5-oxo-5H-dibenzo[a,d]cycloheptane for the 2-carboxy-5-oxo-5H-dibenzo-[a,d]cycloheptene, there is prepared 2-(5-oxo-5H-dibenzo[a,d]cycloheptan-2-yl)prop-1-en-3-ol.

EXAMPLE I 0.25 G. of 2-(5-oxo-5H-dibenzo[a,d]cyclohepten-2-yl)-propionyl chloride (as prepared in Preparation 10 above) is dissolved in 4 ml. of diglyme and the solution cooled to −78°C. 3.5 Ml. of 0.045 molar lithium aluminum tri-tertiary butoxy hydride in diglyme is added, in 0.5 ml. portions over the course of 1 hour, to this solution. The mixture is warmed to room temperature and poured into water and extracted with ether. The extract is washed, dried and evaporated to give a crude product to which is added a solution of 0.106 g. of dianilinoethane and 0.072 g. of acetic acid in 5 ml. of methanol. The mixture is left for 1 hour than decanted from the insoluble product, α-(1,3-diphenyl-2-imidazolidinyl) 2-ethyl-5-oxo-5H-dibenzo[a,d]cycloheptene [a gum; nmr spectrum in deuterochloroform relative to tetramethylsilane: 1.47 (doublet, CHCH$_3$), 5.77 (singlet, N-CH-N) acid 6.90 ppm (singlet, 10H, 11H). This compound is dissolved in 10 ml. of ether and the solution shaken with dilute hydrochloric acid. The ethereal layer is dried and evaporated to give 2-(5-oxo-5H-dibenzo[a,d]cyclohepten-2-yl)propanal [a gum; nmr spectrum in deuterochloroform relative to tetramethylsilane: 0.98 (doublet, CHCH$_3$), 3.78 (quartet, CHCH$_3$), 7.02 (singlet, 10H, 11H) and 9.72 ppm (doublet, CHO); mass spectrum: 262 (M+) 233, 205].

In similar manner substituting the appropriate acid chlorides prepared in Preparation 10 for the 2-(5oxo-5H-dibenzo[a,d]cyclohepten-2-yl)propionyl chloride, the following compounds are prepared:

2-(5-oxo-5H-dibenzo[a,d]cyclohepten-2yl)ethanal,
2-(5-oxo-5H-dibenzo[a,d]cyclohepten-2-yl)butanal.
2-(5-oxo-5H-dibenzo[a,d]cycloheptan-2-yl)ethanal,
2-(5-oxo-5H-dibenzo[a,d]cycloheptan-2-yl)propanal, and
2-(5-oxo-5H-dibenzo[a,d]cycloheptan-2-yl)butanal.

EXAMPLE II

The procedure of Example 1 is repeated using (d) 2-(5-oxo-5H-dibenzo[a,d]cyclohepten-2-yl)propionyl chloride (also as prepared in Preparation 10) to obtain the optically active intermediate α-(1,3-diphenyl-2-imidazolidinyl) 2-ethyl-5-oxo-5H-dibenzo[a,d]cycloheptene (m.p. 81°–89°) which is decomposed as described above to afford (d) 2-(5-oxo-5H-dibenzo[a,d]cyclohepten-2-yl)propanal [a gum; [α]$_D$ + 66.7° (5 mg./ml. in chloroform)].

In similar manner using the other optically active acid chlorides prepared in Preparation 10, the corresponding optically active aldehydes are prepared.

EXAMPLE III 0.37 Ml. of pyridine is added to 15 ml. of methylene chloride, followed by 0.235 g. of chromium trioxide. The mixture is stirred for 15 minutes and to it is added 0.078 g. of 2-(5-oxo-5H-dibenzo[a,d]cycloheptan-2-yl)propan-1-ol (as prepared in Preparation 11 above). After 5 minutes, the mixture is poured into ether and the solution washed with 10% hydrochloric acid, aqueous sodium bicarbonate and water, then dried and chromatographed on a silica gel column. The eluate is evaporated to afford 2-(5-oxo:5H-dibenzo[a,d]-cycloheptan-2-yl)propanal [a gum; nmr spectrum in deuterochloroform relative to tetramethylsilane, 1.47 (doublet, CH$_3$), 3.20 (singlet, 10H, 11H) and 9.69 ppm (doublet, CHO); mass spectrum: 264 (m+) 235, 207].

In similar manner using the other alkanols prepared in Preparations 11 and 12 the corresponding aldehydes are prepared, including 2-(5H-dibenzo[a,d]cyclohepten-2-yl)propenal and 2-(5-oxo-5H-dibenzo[a,d]cycloheptan-2-yl)propenal.

EXAMPLE IV 0.200 G. of 2-(5-oxo-5-H-dibenzo[a,d]cyclohepten-2-yl)propanal is dissolved in 10 ml. of methanol and 20 ml. of tetrahydrofuran, and 1 drop of 60% aqueous perchloric acid is added. The mixture is left for 1 hour then 2 drops of pyridine are added and the mixture added to water and ether. The organic layer is washed with water, dried and evaporated and the residue chromatographed on 5 gm. of silica gel, eluting with 50:50:1 hexane:ether:triethylamine to afford 1,1-dimethoxy 2-(5-oxo-5H-dibenzo[a,d]cyclohepten-2-yl)propane.

In similar manner substituting the other aldehydes of Examples I and II, the corresponding 1,1-dimethoxy acetals thereof are prepared.

Also in similar manner, substituting ethanol, n-propanol, i-propanol, n-butanol, i-butanol, n-pentanol, i-pentanol, n-hexanol or i-hexanol for the methaol, the corresponding 1,1-dialkoxy acetals of the aldehydes of Examples I and Ii are prepared.

EXAMPLE V

To a solution of 0.288 g. of 2-(5-oxo-5H-dibenzo[a,d]-cyclohepten-2-yl)propanal in 4 ml. of ethanol is added a solution of 0.12 g. of hydroxylamine hydrochloride and 0.11 g. of sodium hydroxide in 0.4 ml. of water. The mixture is refluxed briefly, then acidified with dilute hydrochloric acid and extracted with ethyl acetate. The extract is washed, dried and evaporated to yield a crude product which is chromatographed on silica gel, eluting with chloroform:methanol (19:1) to afford 2-(5-oxo-5H-dibenzo[a,d]cycloheptan-2-yl)propanal oxime.

In a similar manner, substituting any of the other aldehydes prepared in Examples I and II for the 2-(-(5-oxo-5H-dibenzo[a,d]cyclohepten-2-yl)propanal used above, the corresponding aldehyde oximes are prepared.

EXAMPLE VI

To a solution of 0.288 g. of 2-(5-oxo-5H-dibenzo[a,d]cyclohepten-2-yl)propanal in 3 ml. of methanol is added a solution of 0.111 g. of semicarbazide hydrochloride in 0.5 ml. of water, followed by 1 drop of pyridine. The mixture is refluxed briefly and then poured into water. The product is extracted with ethyl acetate and the extract washed, dried and evaporated to afford, upon crystallization from ethyl acetate/hexane, 2-(5-oxo-5H-dibenzo[a,d]-cyclohepten-2-yl)propanal semicarbazone.

In similar manner, substituting any of the other aldedehydes prepared in Examples I and II for the 2-(5-oxo-5H-dibenzo[a,d]cyclohepten-2yl)propanal used above, the corresponding aldehyde semicarbazones are prepared.

EXAMPLE VII

The procedure of Example IV is repeated substituting ethylene glycol for the methanol to afford 1,1-ethylenedioxy-2-(5-oxo-5H-dibenzo[a,d]cyclohepten-2-yl)propane.

In a similar manner substituting ay of the other aldehydes prepared in Examples I and II for the 2-(5-oxo-5-dibenzo[a,d]cyclohepten-2-yl)propanal, the corresponding 1,1-ethylenedioxy-cyclic acetals are prepared.

Also in similar manner substituting 1,3-propylene glycol, 2,2-dimethylpropylene glycol or 1,4-butanediol for the ethylene glycol, and using any of the aldehydes prepared in Example I and II, the corresponding cyclic acetals of the particular aldehyde utilized are prepared.

EXAMPLE VIII

A solution of 2.62 g. of 2-(5-oxo-5H-dibenzo[a,d]cyclohepten-2-yl)propanal in 50 ml. of ether is shaken with 25 ml. of saturated aqueous sodium bisulfite. The solution is filtered and the residue washed with ether and water, then dried to yield the sodium bisulfite addition product of 2-(5-oxo-5-H-dibenzo[a,d]cyclohepten-2-yl)propanal.

In a similar manner substituting potassium bisulfite for the sodium bisulfite utilized above, the potassium bisulfite addition product of 2-(5-oxo-5H-dibenzo[a,d-]cyclohepten-2-yl)propanal is prepared.

Also in similar manner, using any of the other aldehydes prepared in Examples I and II, and either sodium bisulfite or potassium bisulfite, the corresponding sodium bisulfite or potassium bisulfite addition products are prepared.

EXAMPLE IX

A solution is prepared having 100 mg. of d 2-(5-oxo-5H-dibenzo[a,d]cyclohepten-2-yl)propanal dissolved per ml. of 70% propylene glycol -30% normal saline solution.

EXAMPLE X

Example IX is repeated except dl 2-(5-oxo-5H-dibenzo[ [a,d]cyclohepten-2-yl)propanal and 2-(5-oxo-5H-dibenzo[a,d]-cyclohept-2-yl)propanal are respectively substituted for the d 2-(5-oxo-5H-dibenzo[a,d]cyclohepten-2-yl)propanal of Example IX.

EXAMPLE XI

A suspension is prepared having 100 mg. of d 2-(5-oxo-5H-dibenzo[a,d]cyclohepten-2-yl)propanal per ml. of normal saline solution containing 0.1% Tween 80 (sorbitan monooleate polyoxyethylene; a product of Atlas Chemical Industries, Inc.).

EXAMPLE XII

| Ingredients | Quantity per tablet, mgs. |
| --- | --- |
| d 2- (5-oxo-5H-dibenzo[a,d]-cyclohepten-2-yl)propanal | 300 |
| cornstarch (paste) | 50 |
| Magnesium stearate | 0.8 |
| lactose | to 500 |

The above ingredients are thoroughly mixed and pressed into single scored tablets.

| Ingredients | Quantity per tablet, mgs. |
| --- | --- |
| d 2- (5-oxo-5H-dibenzo[a,d]-cyclohepten-2-yl)propanal | 250 |
| cornstarch | 38 |
| magnesium stearate | 0.76 |
| polyvinylpyrrolidone | 17 |
| lactose | to 380 |

The above ingredients are mixed intimately and pressed into single scored tablets.

EXAMPLE XIV

| Ingredients | Quantity per capsule, mgs. |
| --- | --- |
| 2-(5-oxo-5H-dibenzo[a,d]-cyclohepten-2-yl)propanal | 250 |
| cornstarch | 38 |
| lactose | to 380 |

The above ingredients are mixed and introduced into a hard-shell gelatin capsule.

EXAMPLE XV

A suppository totaling 2.8 grams is prepared having the following composition:

| | |
| --- | --- |
| d 2-(5-oxo-5H-dibenzo[a,d]cyclo-hepten-2-yl)propanal | 150–500 mg. |
| Witepsol H-15 (triglycerides of saturated vegetable fatty acids; a product of Riches-Nelson, Inc., New York, N.Y.) | balance |

| Ingredients | Quantity per tablet, wt.% |
| --- | --- |
| d 2- (5-oxo-5H-dibenzo[a,d]-cyclohepten-2-yl)propanal | 68–75% |
| Avicel (FMC Corp.) | 15–28% |
| Cabosil (Cabot Corp.) | 0.5–1% |
| magnesium stearate | 0.5–2% |
| lactose | 0–15% |

15

The above ingredients are thoroughly mixed and pressed into single scored 400 mg. tablets.

EXAMPLE XVII

The anti-inflammatory activity of the following compounds embraced within this invention was compared with the activity of phenylbutazone by means of the carrageenin-induced rat paw inflammation test described below.

TEST FOR ANTI-INFLAMMATORY ACTIVITY UTILIZING CARRAGEENIN INDUCED PAW INFLAMMATION IN THE RAT

Materials and Methods - Femal rats weighing 80–90 grams are used. The test materials are given at hour 0 orally by gavage in 1 ml. aqueous vehicle. At hour 1, 0.05 ml. of a 1% solution (in 0.0% NaCl) of carrageenin is injected into the right hind paw. This injection causes an inflammation of the paw. The rats are sacrificed at hour 4, at which time both hind paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

The results of these tests are summarized in the following table:

| Compound | Oral Anti-Inflammatory Activity (Phenylbutazone = 1) |
|---|---|
| d 2-(5-oxo-5H-dibenzo[a,d]-cyclohepten-2-yl)propanal | 8 |

This compound was also tested for analgesic activity in the well-known mouse analgesic (anti-writhing) assay and was found to be about three times as potent as aspirin.

While the present invention has been described with reference to specific embodiments thereof, it should be understood by those skilled in this art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

What is claimed is:

1. A compound selected from the group of compounds represented by the formula:

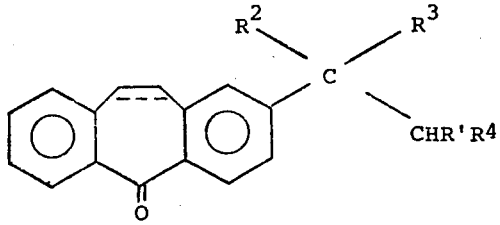

where one of $R^2$ and $R^3$ is hydrogen and the other is hydrogen, methyl, ethyl or together $R^2$ and $R^3$ are methylene; one of $R'$ and $R^4$ is —OH and the other is —$SO_3Y$ where Y is sodium or potassium, and the dotted line refers to an optional, additional bond between the carbon atoms at the 10- and 11-positions.

2. The compound of claim 1 where both $R^2$ and $R^3$ are hydrogen.

3. The compound of claim 1 where there is a single bond between the carbon atoms at the 10- and 11-positions.

4. The compound of claim 1 where there is a double bond between the carbon atoms at the 10- and 11-positions.

5. A compound selected from the group of compounds represented by the formula:

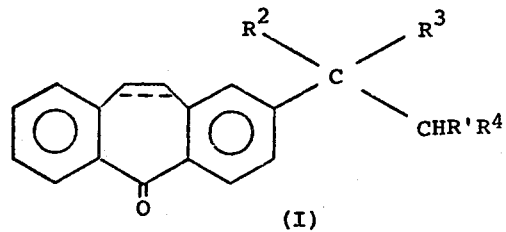

where one of $R^2$ and $R^3$ is hydrogen and the other is methyl; one of $R'$ and $R^4$ is -OH and the other is -$SO_3Y$ where Y is sodium or potassium, and the dotted line refers to an optional, additional bond between the carbon atoms at the 10- and 11-positions.

6. The compounds of claim 5 where there is a single bond between the carbon atoms at the 10- and 11-positions.

7. The compounds of claim 5 where there is a double bond between the carbon atoms at the 10- and 11-positions.

8. A composition for treating inflammation, pain or pyrexia in mammals comprising a pharmaceutically acceptable non-toxic excipient and a therapeutically effective amount of a compound represented by the formula:

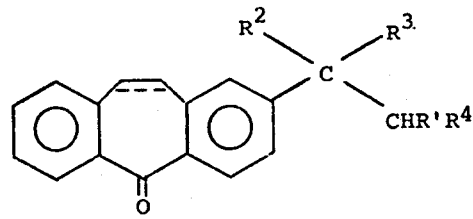

where one of $R^2$ and $R^3$ is hydrogen and the other is hydrogen, methyl, or ethyl, or together $R^2$ and $R^3$ are methylene; one of $R'$ and $R^4$ is -OH and the other is -$SO_3Y$ where Y is sodium or potassium, and the dotted line refers to an optional, additional bond between the carbon atoms at the 10- and 11-positions.

9. The composition of claim 8 wherein one of $R^2$ and $R^3$ is hydrogen and the other is methyl.

10. The method of treating inflammation, pain, or pyrexia in mammals which comprises administering to a mammal suffering therefrom a therapeutically effective amount of a compound represented by the formula:

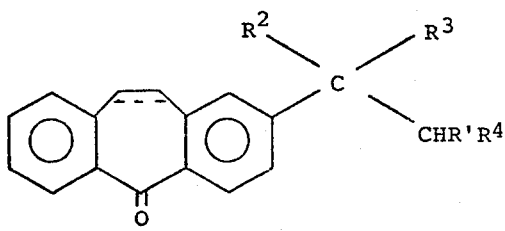

ps where one of $R^2$ and $R^3$ is hydrogen and the other is hydrogen, methyl, or ethyl, or together $R^2$ and $R^3$ are methylene; one of $R'$ and $R^4$ is —OH and the other is $-SO_3Y$ where Y is sodium or potassium, and the dotted line refers to an optional, additional bond between the carbon atoms at the 10- and 11-positions.

11. The method of claim 10 wherein one of $R^2$ and $R^3$ is hydrogen and the other is methyl.

12. The compound of claim 1 where one of $R^2$ and $R^3$ is hydrogen and the other is ethyl.

13. The compound of claim 1 where $R^2$ and $R^3$ are methylene.

14. The compound of claim 5 wherein said compound is the sodium bisulfite addition product of 2-(5-oxo-5H-dibenzo[a,d]cyclohepten-2-yl)propanal.

15. The compound of claim 5 wherein said compound is the potassium bisulfite addition product of 2-(5-oxo-5H-dibenzo[a,d]-cyclohepten-2-yl)propanal.

16. The compound of claim 5 wherein said compound is the sodium bisulfite addition product of 2-(5-oxo-5H-dibenzo[a,d]-cycloheptan-2-yl)propanal.

17. The compound of claim 5 wherein said compound is the potassium bisulfite addition product of 2-(5-oxo-5H-dibenzo[a,d]-cycloheptan-2-yl)propanal.

18. The composition of claim 8 wherein $R^2$ and $R^3$ are both hydrogen.

19. The composition of claim 8 wherein one of $R^2$ and $R^3$ is hydrogen and the other is ethyl.

20. The composition of claim 8 wherein $R^2$ and $R^3$ are methylene.

21. The composition of claim 8 where said compound has a single bond between the carbon atoms at the 10- and 11-positions.

22. The composition of claim 8 wherein said compound has a double bond between the carbon atoms at the 10- and 11-positions.

23. The composition of claim 9 wherein said compound has a single bond between the carbon atom at the 10- and 11-positions.

24. The composition of claim 9 wherein said compound has a double bond between the carbon atoms at the 10- and 11-positions.

25. The composition of claim 8 wherein said compound is the sodium bisulfite addition product of 2-(5-oxo-5H-dibenzo[a,d]-cyclohepten-2-yl)propanal.

26. The composition of claim 8 wherein said compound is the potassium bisulfite addition product of 2-(5-oxo-5H-dibenzo[a,d]cyclohepten-2yl)propanal.

27. The composition of claim 8 wherein said compound is the sodium bisulfite addition product of 2-(5-oxo-5H-dibenzo[a,d]-cycloheptan-2-yl)propanal.

28. The composition of claim 8 wherein said compound is the potassium bisulfite addition product of 2-(5-oxo-5H-dibenzo[a,d]cycloheptan-2-yl)propanal.

29. The method of claim 16 wherein $R^2$ and $R^3$ are both hydrogen.

30. The method of claim 10 wherein one of $R^2$ and $R^3$ is hydrogen and the other is ethyl.

31. The method of claim 10 wherein $R^2$ and $R^3$ are methylene.

32. The method of claim 10 wherein said compound has a single bond between the carbon atoms at the 10- and 11-positions.

33. The method of claim 10 wherein said compound has a double bond between the carbon atoms at the 10- and 11-positions.

34. The method of claim 1 wherein said compound has a single bond between the carbon atoms at the 10- and 11-positions.

35. The method of claim 11 wherein said compound has a double bond between the carbon atoms at the 10- and 11-positions.

36. The method of claim 11 wherein said compound is the sodium bisulfite addition product of 2-(5-oxo-5H-dibenzo[a,d]cyclohepten-2-yl)propanal.

37. The method of claim 11 wherein said compound is the potassium bisulfite addition product of 2-(5-oxo-5H-dibenzo[a,d]cyclohepten-2-yl)propanal.

* * * * *